(12) United States Patent
Kumar et al.

(10) Patent No.: US 11,837,337 B2
(45) Date of Patent: Dec. 5, 2023

(54) VOICE-ACTIVATED AMBULANCE BOOKING

(71) Applicant: CERNER INNOVATION, INC., Kansas City, KS (US)

(72) Inventors: Vikas S. Kumar, Karnataka (IN); Amar Mavinagidad, Karnataka (IN); Deepika Roy, Karnataka (IN); Soumen Tapadar, Karnataka (IN)

(73) Assignee: Cerner Innovation, Inc., Kansas City, MO (US)

( * ) Notice: Subject to any disclaimer, the term of this patent is extended or adjusted under 35 U.S.C. 154(b) by 515 days.

(21) Appl. No.: 16/127,609

(22) Filed: Sep. 11, 2018

(65) Prior Publication Data

US 2020/0082917 A1    Mar. 12, 2020

(51) Int. Cl.
*G16H 10/20*  (2018.01)
*G06F 3/16*   (2006.01)
*G16H 10/60*  (2018.01)
*G06Q 50/30*  (2012.01)

(52) U.S. Cl.
CPC .......... *G16H 10/20* (2018.01); *G06F 3/167* (2013.01); *G06Q 50/30* (2013.01); *G16H 10/60* (2018.01)

(58) Field of Classification Search
CPC ........ G16H 10/20; G16H 10/60; G06F 3/167; G06Q 50/30
See application file for complete search history.

(56) References Cited

U.S. PATENT DOCUMENTS

| 10,943,463 | B1 * | 3/2021 | Clark | G08B 21/0438 |
| 2008/0081646 | A1 * | 4/2008 | Morin | H04W 4/029 455/466 |
| 2010/0190479 | A1 * | 7/2010 | Scott | G06F 40/58 455/414.1 |
| 2014/0370841 | A1 * | 12/2014 | Roberts | H04M 1/72536 455/404.2 |
| 2016/0140299 | A1 * | 5/2016 | Al Harbi | G06F 19/00 705/2 |
| 2017/0344707 | A1 * | 11/2017 | Patel | G16H 40/20 |

OTHER PUBLICATIONS

M. M. Rahman, J. R. Mou, K. Tara and M. I. Sarkar, "Real time Google map and Arduino based vehicle tracking system," 2016 2nd International Conference on Electrical, Computer & Telecommunication Engineering (ICECTE), Rajshahi, Bangladesh, 2016, pp. 1-4, (Year: 2016).*

* cited by examiner

*Primary Examiner* — Fonya M Long
*Assistant Examiner* — Anthony Balaj
(74) *Attorney, Agent, or Firm* — Invoke (57) ABSTRACT

Embodiments of the present disclosure relate to systems, methods, and user interfaces for providing voice-activated ambulance booking. Initially, a non-medical user initiates a workflow, via a voice command, that enables the user to provide information about a patient that can be utilized to prioritize the booking of ambulances for patients. Upon providing the initial voice command, the workflow is provided, via a user interface of the user device. The workflow comprises a series of questions corresponding to a status of the patient that can easily be answered merely by observing the patient (e.g., is the patient conscious, is the patient breathing, is the patient bleeding). Based on responses provided by the user, an ambulance is requested for the patient. User device vitals including battery charge levels and signal strength can be used to resolve conflicts if multiple requests are made.

14 Claims, 7 Drawing Sheets

VOICE-ACTIVATED AMBULANCE BOOKING

BACKGROUND

Medical emergencies often demand immediate lifesaving interventions or time-sensitive treatments. Generally, finding an ambulance involves calling an operational center (e.g., 911) and providing an address. In turn, the operational center may connect the caller to the most appropriate ambulance based on the location and availability of ambulances. Current systems allow the user to request the closest available ambulance by using geo-location information provided by a user device (e.g., a mobile phone). In some instances, however, the user device may be locked and the caller may not be able to operate the device. In other instances, the user may be injured and unable to operate the device. Even when a caller is able to call the operational center, the user may fail to properly convey the status of the patient or the user device that may affect prioritization of the call and allocation of resources (e.g., the ambulance).

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for providing voice-activated ambulance booking. More particularly, embodiments of the present disclosure empower a non-medical user to initiate a workflow, via a voice command, that enables the user to provide information about a patient that can be utilized to prioritize the booking of ambulances for patients. In embodiments, the voice command may initiate the workflow even if a user device is locked. Upon providing the initial voice command, the workflow is provided, via a user interface of the user device. The workflow comprises a series of questions corresponding to a status of the patient that can easily be answered merely by observing the patient (e.g., is the patient conscious, is the patient breathing, is the patient bleeding). Based on responses provided by the user, an ambulance is requested for the patient. In embodiments, user device vitals including battery charge levels and signal strength can be used to resolve conflicts if multiple requests are made. In some embodiments, the workflow can be initiated even if the user device is in an offline mode. Moreover, the workflow can be integrated with other ambulance booking services and/or into an electronic medical record (EMR) of the patient.

BRIEF DESCRIPTION OF THE SEVERAL VIEWS OF THE DRAWINGS

The patent or application file contains at least one drawing executed in color. The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, medical emergencies often demand immediate lifesaving interventions or time-sensitive treatments. Generally, finding an ambulance involves calling an operational center (e.g., 911) and providing an address. In turn, the operational center may connect the caller to the most appropriate ambulance based on the location and availability of ambulances. Current systems allow the user to request the closest available ambulance by using geo-location information provided by a user device (e.g., a mobile phone). In some instances, however, the user device may be locked and the caller may not be able to operate the device. In other instances, the user may be injured and unable to operate the device. Even when a caller is able to call the operational center, the user may fail to properly convey the status of the patient or the user device that may affect prioritization of the call and allocation of resources (e.g., the ambulance).

Embodiments of the present disclosure relate to systems, methods, and user interfaces for providing voice-activated ambulance booking. More particularly, embodiments of the present disclosure empower a non-medical user to initiate a workflow, via a voice command, that enables the user to provide information about a patient that can be utilized to prioritize the booking of ambulances for patients. In embodiments, the voice command may initiate the workflow even if a user device is locked. Upon providing the initial voice command, the workflow is provided, via a user interface of the user device. The workflow comprises a series of questions corresponding to a status of the patient that can easily be answered merely by observing the patient (e.g., is the patient conscious, is the patient breathing, is the patient bleeding). Based on responses provided by the user, an ambulance is requested for the patient. In embodiments, mobile device vitals including battery charge levels, signal strength, and the location of the user device from the nearest hospital can be used to resolve conflicts if multiple requests are made. In some embodiments, the workflow can be initiated even if the user device is in an offline mode.

Moreover, the workflow can be integrated with other ambulance booking services and/or into an electronic medical record (EMR) of the patient.

Accordingly, one embodiment of the present disclosure is directed to one or more computer storage media having computer-executable instructions embodied thereon that, when executed by a computer, causes the computer to perform operations for providing voice-activated ambulance booking. The operations include receiving, at a user device, a voice command from a user. The voice command initiates a workflow that enables the user to provide information about a patient to a booking engine. The operations also include providing the workflow to the user, via a user interface of the user device. The workflow comprises a series of questions corresponding to a status of the patient. The operations further include requesting an ambulance for the patient. The ambulance is requested based on responses from the user, via the user interface of the user device, to the series of questions, and a detected location of the user device.

In another embodiment, the present disclosure directed to a computerized method providing voice-activated ambulance booking. The method comprises receiving, at a user device, a voice command from a user. The voice command initiates a workflow that enables the user to provide information about a patient to a booking engine. The method also comprises providing the workflow to the user, via a user interface of the user device. The workflow comprises a series of questions corresponding to a status of the patient. The method further comprises requesting an ambulance for the patient. The ambulance is requested based on responses from the user, via the user interface of the user device, to the series of questions, and a detected location of the user device. The method also comprises identifying the ambulance for the patient that is available. The method further comprises determining a plurality of requests have been received from other patients. The method also comprises prioritizing requests from the patient and the other patients based on responses of the patient and the other patients to the series of questions.

In yet another embodiment, the present disclosure is directed to a system for providing voice-activated ambulance booking. The system comprises a processor; and a computer storage medium storing computer-usable instructions that, when used by the processor, cause the processor to: receive, at a user device, a voice command from a user, the voice command initiating a workflow that enables the user to provide information about a patient to a booking engine; provide the workflow to the user, via a user interface of the user device, the workflow comprising a series of questions corresponding to a status of the patient; request an ambulance for the patient, the ambulance requested based on responses from the user, via the user interface of the user device, to the series of questions, and a detected location of the user device; and identify the ambulance for the patient that is available.

Figure 1:
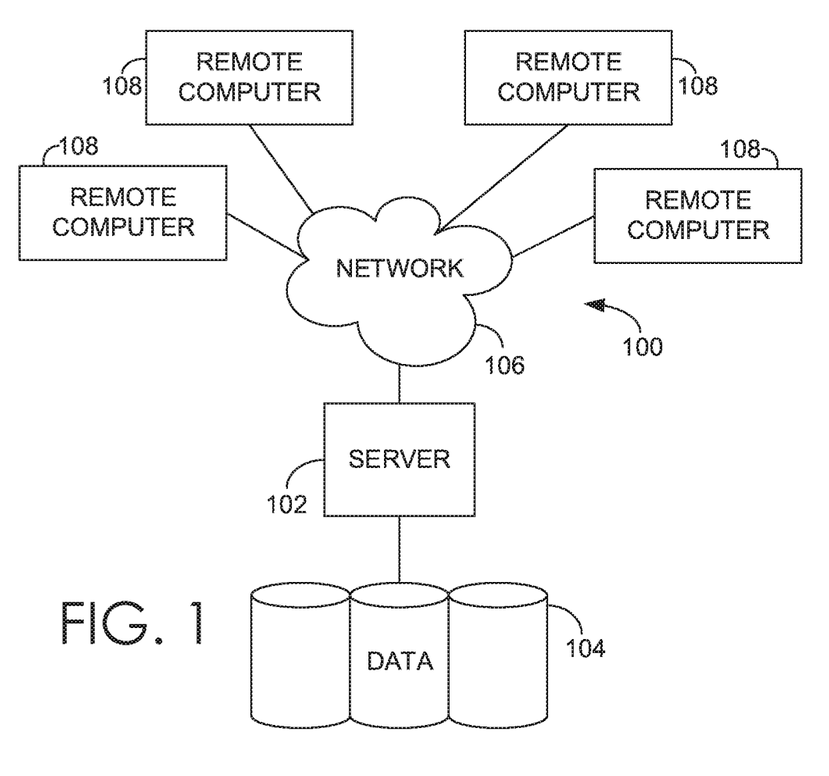
FIG. 1 is a block diagram of an exemplary operating environment suitable to implement embodiments of the present invention.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
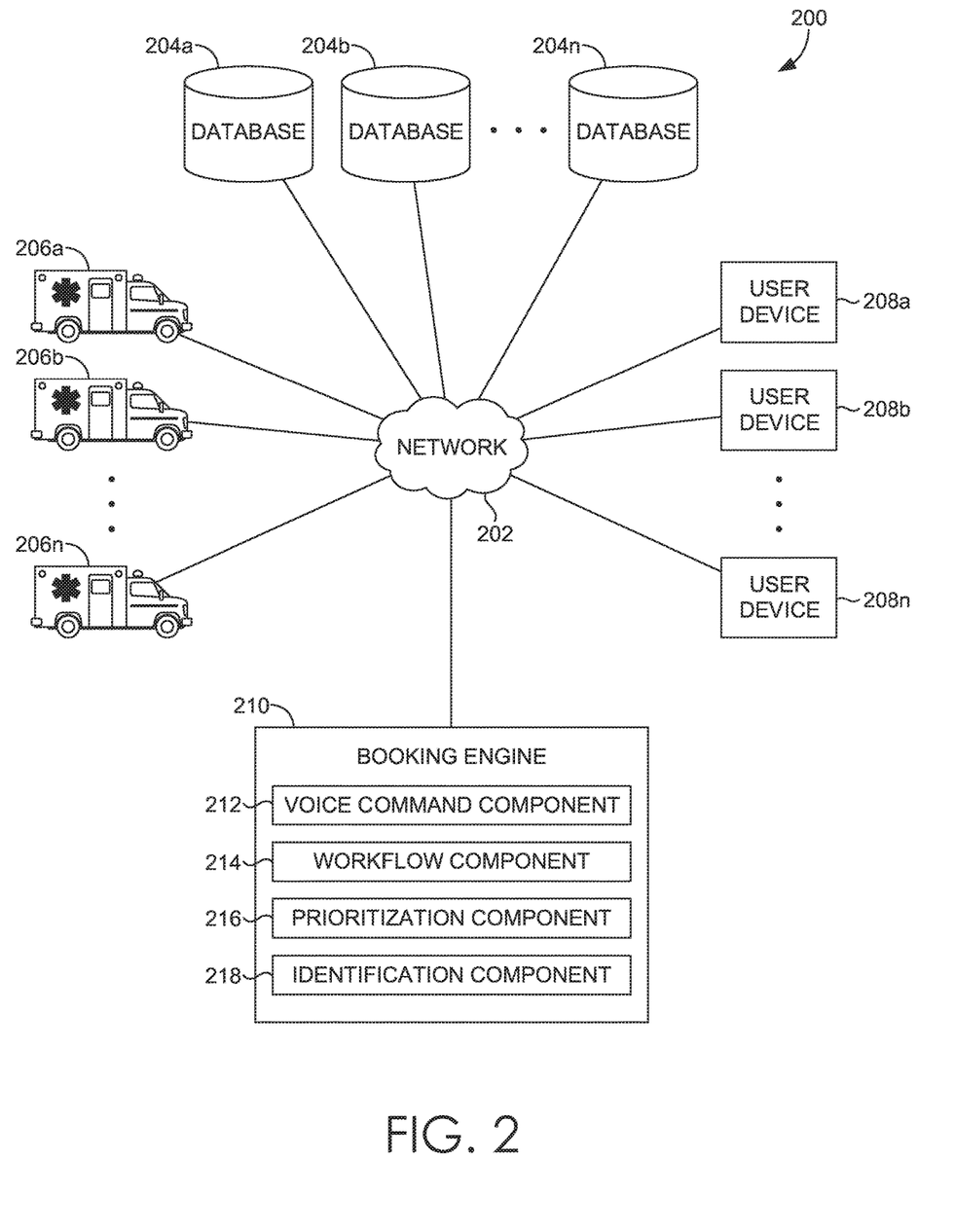
FIG. 2 depicts an exemplary framework of a voice-activated ambulance booking system suitable to implement embodiments of the present invention.

Turning now to FIG. 2, an exemplary framework of a voice-activated ambulance booking system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The voice-activated ambulance booking system 200 may be implemented via any type of computing device, such as computing device 100 described above with reference to FIG. 1, for example.

The voice-activated ambulance booking system 200 generally operates to provide voice-activated ambulance booking. More particularly, the voice-activated ambulance booking system 200 empowers a non-medical user to initiate a workflow, via a voice command, that enables the user to provide information about a patient that can be utilized to prioritize the booking of ambulances for patients. Upon a user providing the initial voice command, the workflow is provided by the voice-activated ambulance booking system 200, via a user interface of the user device. The workflow comprises a series of questions corresponding to a status of the patient that can easily be answered merely by observing the patient (e.g., is the patient conscious, is the patient breathing, is the patient bleeding). Based on responses provided by the user, an ambulance is requested for the patient.

As shown in FIG. 2, the voice-activated ambulance booking system 200 includes, among other components not shown, database(s) 204a-204n, ambulance(s) 206a-206n, user device(s) 208a-208n, and booking engine 210. It should be understood that the voice-activated ambulance booking system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network 202, which may include, without limitation, one or more local area networks (LANs) and/or wide area networks (WANs). Such networking environments are commonplace in offices, enterprise-wide computer networks, intranets, and the Internet. It should be understood that any number of booking engines may be employed within the voice-activated ambulance booking system 200 within the scope of the present disclosure. Each may comprise a single device or multiple devices cooperating in a distributed environment. For instance, the booking engine 210 (or any of its components: voice command component 212, workflow component 214, prioritization component 216, identification component 220) may be provided via multiple devices arranged in a distributed environment that collectively provide the functionality described herein. In other embodiments, a single device may provide the functionality of multiple components of the voice-activated ambulance booking system 200. For example, a single device may provide the booking engine 210 and/or the database(s) 204a-204n. In some embodiments, some or all functionality provided by the booking engine 210 (or any of its components) and/or the database(s) 204a-204n may be provided by a user device. Additionally, other components not shown may also be included within the network environment.

Generally, the booking engine 210 enables a user to initiate a workflow on a user device, by voice-command, that enables the user to request and book an ambulance for a patient. In embodiments, the voice command may initiate the workflow even if a user device is locked. Upon providing the initial voice command, the workflow is provided, via a user interface of the user device.

Although the workflow is described herein as being provided via a user interface, it is contemplated that the user interface may not be limited to a visual workflow. For example, the workflow may be an interaction between voice commands received from a user and voice responses provided via the user device by the application. The workflow may also be an interaction between a combination of voice inputs and outputs and visual inputs and outputs. The voice commands and voice responses enable the application to be utilized even when the user device is in a locked mode. In some embodiments, the voice command that initiates the workflow when the user device is locked enables the remainder of the workflow via voice inputs and outputs or visual inputs and outputs, or a combination of both. In this way, the initial voice command serves to unlock the user device for the purpose of utilizing the workflow.

The workflow comprises a series of questions corresponding to a status of the patient that can easily be answered merely by observing the patient (e.g., is the patient conscious, is the patient breathing, is the patient bleeding). Based on responses provided by the user, an ambulance is requested for the patient. In embodiments, mobile device vitals including battery charge levels, signal strength, and the location of the user device from the nearest hospital can be used to resolve conflicts if multiple requests are made. In some embodiments, the workflow can be initiated even if the user device is in an offline mode. Moreover, the workflow can be integrated with other ambulance booking services and/or into an electronic medical record (EMR) of the patient.

As described above, the booking engine 210 includes several components including voice command component 212, workflow component 214, prioritization component 216, and identification component 220.

The voice command component 212 generally receives, from a user device, a voice command from a person. The voice command initiates a workflow that enables the person to provide information about a patient to a booking engine.

The workflow component 214 generally provides the workflow to the user, via a user interface of the user device. The workflow comprises a series of questions corresponding to a status of the patient. For example, the workflow component 214 may prompt the user, via the user interface of the user device, to provide information corresponding to the consciousness, breathing, and/or bleeding status of the patient.

The prioritization component 216 generally requests an ambulance for the patient. The ambulance is requested based on responses from the user, via the user interface of the user device, to the series of questions, and a detected location of the user device.

In an embodiment, the prioritization component 216 determines a plurality of ambulances are available for a single user request. Ambulances that have an outstanding request from another patient received prior to the current request from the patient are eliminated from consideration by the prioritization component 216.

In another embodiment, the prioritization component 216 determines a plurality of requests have been received from other patients and only a single ambulance is available. In this case, the prioritization component 216 prioritizes requests from the patient and the other patients based on responses to the series of questions. As described, the series of questions may comprise breathing status, bleeding status, and/or consciousness status of the patient and the other patients.

Additionally, or alternatively, the prioritization component 216 further prioritizes requests based on battery status of devices making the requests, signal strength of devices making the requests, and/or detected location of the devices.

The identification component 218 generally identifies the ambulance for the patient that is available, best suited, or based on priority information received from prioritization component 216. In some embodiments, the identification component 218 communicates an offer corresponding to the user. The offer may include an estimated time of arrival, estimated costs, insurance coverage information, and the like. In some embodiments, an acknowledgement may be received from the user indicating the user has accepted the offer. The voice-activated ambulance booking may then be confirmed by the identification component 218 to all involved parties. In some embodiments, the identification component 218 enables the user to track the ambulance in real-time, via the user interface, until it reaches the detected location of the user device. Additionally, information of the patient may be communicated by the identification component 218 to an ambulance device, or an EMR that may be accessible by an ambulance device. An emergency contact of the patient may also be notified by the identification component 218. The emergency contact may be provided by the patient at the time of registration with the booking engine 210.

Figure 3:
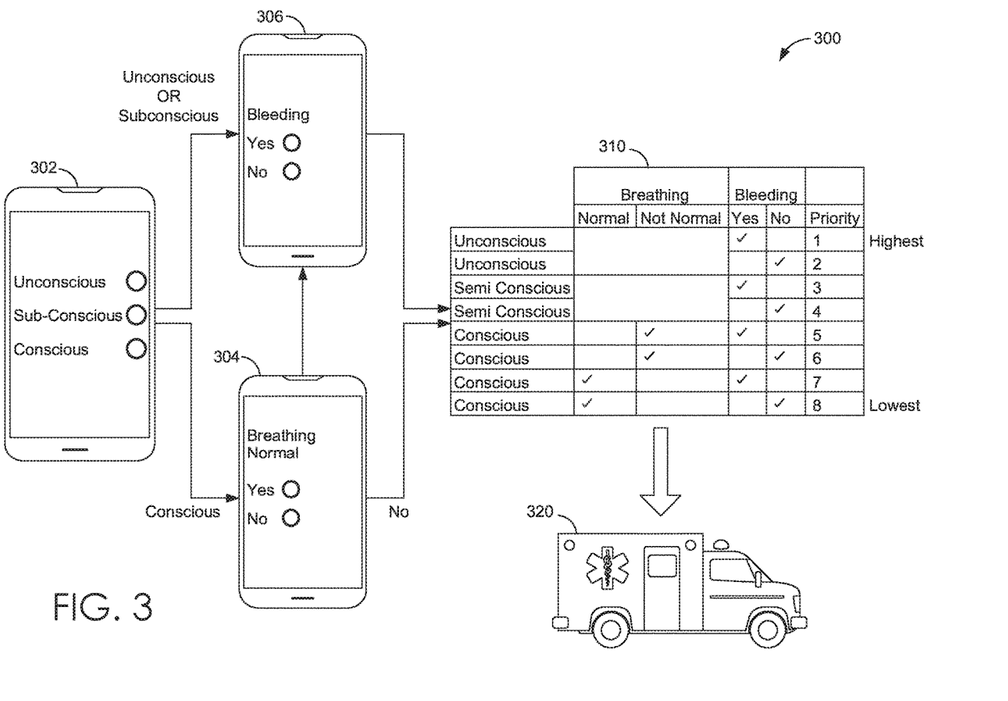
FIG. 3 depicts a flow diagram illustrating the workflow and prioritization for multiple requests from multiple users of the voice-activated ambulance booking system, in accordance with an embodiment of the present invention.

Referring now to FIG. 3, an exemplary flow diagram 300 illustrates the workflow and prioritization for multiple requests from multiple users of the voice-activated ambulance booking system, in accordance with an embodiment of the present invention. Method 300 may be performed by any computing device (such as computing device described with respect to FIG. 1) with access to voice-activated ambulance booking system (such as the one described with respect to FIG. 2) or by one or more components of the voice-activated ambulance booking system.

Initially, as shown at step 302, a user interface prompts a user to indicate the consciousness of the patient. For example, the user may be prompted to indicate whether the patient is unconscious, sub-conscious, or conscious. If the user selects the patient is conscious, the user interface prompts the user, at step 304 to indicate whether the patient is breathing normal. If the user selects the patient is breathing normal or not, or if the user selects the patient is unconscious or sub-conscious in the previous step, the user interface prompts the user to indicate whether the patient is bleeding, at step 306. After the user selects whether the patient is bleeding, at step 306, the responses are provided to the voice-activated ambulance booking system, at step 310, for prioritization. Once a patient and ambulance is selected by the voice-activated ambulance booking system, the selected ambulance is assigned to the selected patient, at step 320. Information provided by the user via the user interface may be provided to the selected ambulance so the clinicians are aware of the patient situation. Similarly, the information may also be provided to the health care facility that the patient is transported to by the ambulance.

Figure 4:
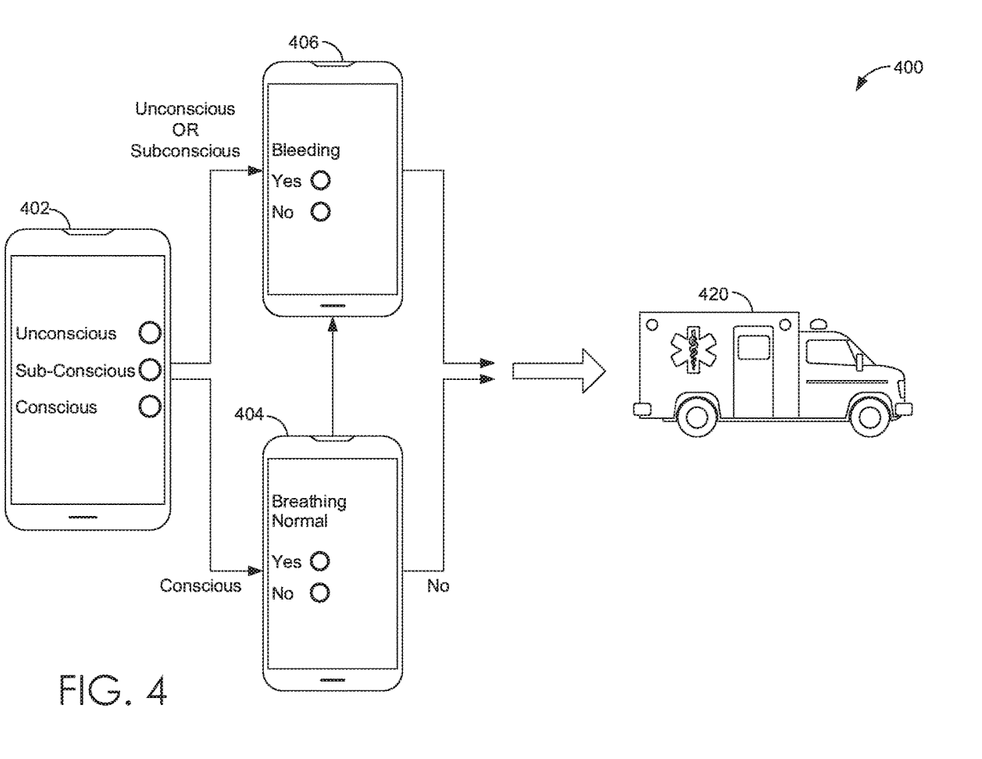
FIG. 4 depicts a flow diagram illustrating the workflow for a single request from a single user of the voice-activated ambulance booking system, in accordance with an embodiment of the present invention.

In FIG. 4, an exemplary flow diagram 400 illustrates the workflow for a single request from a single user of the voice-activated ambulance booking system, in accordance with an embodiment of the present invention. Method 400 may be performed by any computing device (such as computing device described with respect to FIG. 1) with access to voice-activated ambulance booking system (such as the one described with respect to FIG. 2) or by one or more components of the voice-activated ambulance booking system.

Initially, as shown at step 402, a user interface prompts a user to indicate the consciousness of the patient. For example, the user may be prompted to indicate whether the patient is unconscious, sub-conscious, or conscious. If the user selects the patient is conscious, the user interface prompts the user, at step 404 to indicate whether the patient is breathing normal. If the user selects the patient is breathing normal or not, or if the user selects the patient is unconscious or sub-conscious in the previous step, the user interface prompts the user to indicate whether the patient is bleeding, at step 406. After the user selects whether the patient is bleeding, at step 406, the responses are provided to the voice-activated ambulance booking system, and an ambulance is selected by the voice-activated ambulance booking system and assigned to the patient, at step 420.

Figure 5:
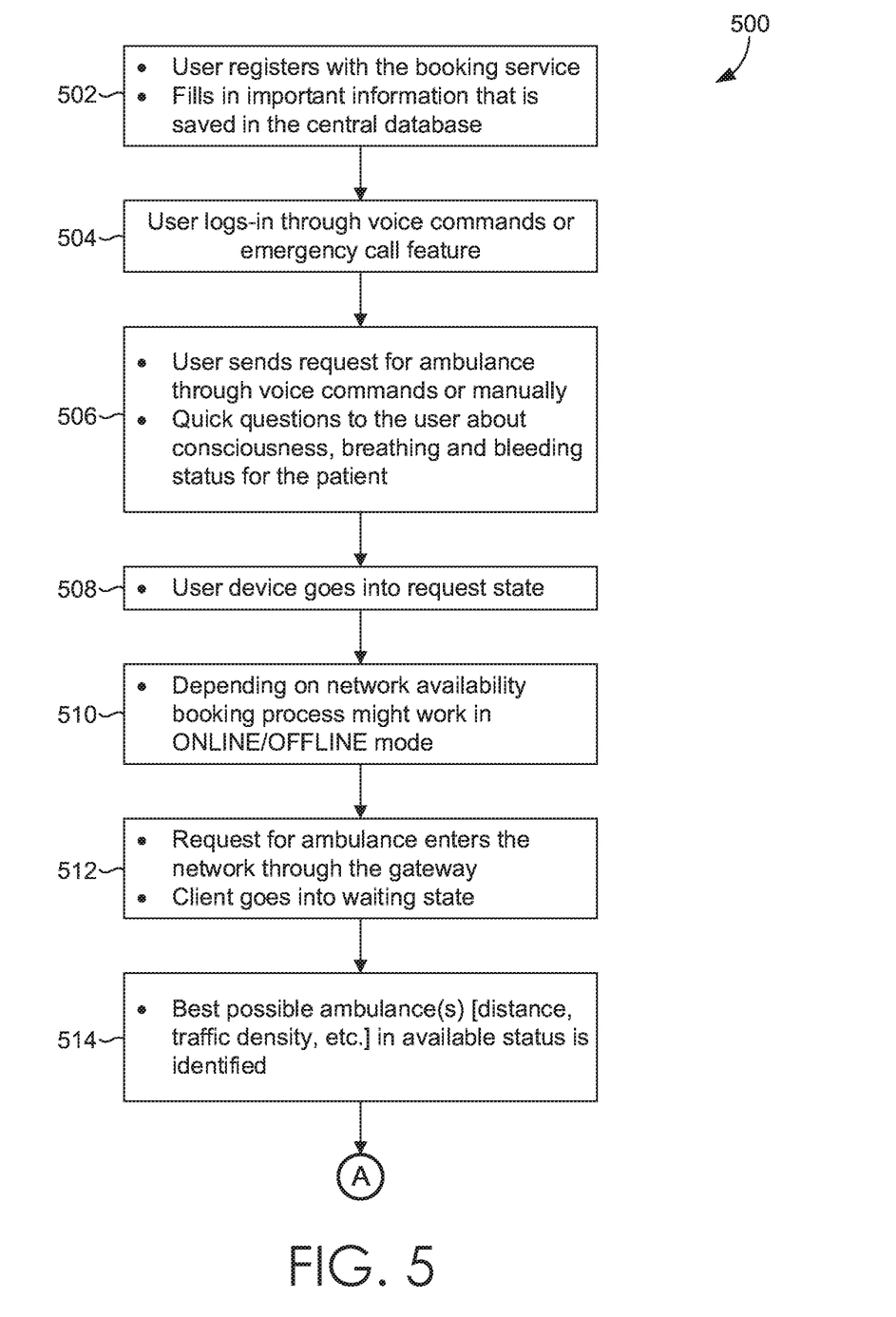
FIG. 5 depicts a flow diagram illustrating voice-activated ambulance booking, in accordance with embodiments of the present invention.

Turning now to FIG. 5, a flow diagram is provided illustrating a method 500 for voice-activated ambulance booking, in accordance with embodiments of the present invention. Method 500 may be performed by any computing device (such as computing device described with respect to FIG. 1) with access to voice-activated ambulance booking system (such as the one described with respect to FIG. 2) or by one or more components of the voice-activated ambulance booking system.

Initially, at step 502, a person registers with the voice-activated ambulance booking system (such as via an online service or application). The person provides important information that is saved in a central database. The important information may include name, address, phone number, age, gender, and the like.

Upon determining an ambulance is needed, a user (e.g., patient or patient's attendant) may initiate or log-in to the voice-activated ambulance booking system, at step 504, with a voice command or emergency call feature via a user device (e.g., a mobile device).

At step 506, the user submits a request for an ambulance through a voice command or manually, via a user interface provided by the voice-activated ambulance booking system (i.e., the client). The user interface provides questions to the user regarding consciousness, breathing, and bleeding status for the patient. Additionally, or alternatively, the questions may be provided audibly to the user. The user may provide answers to the questions via the user interface, or by voice command.

A user corresponding to the user interface provided by the voice-activated ambulance booking system (i.e., the client) enters a request state, at step 508.

Based on network availability, the booking process may work in an online or offline mode, at step 510. For example, in an offline mode, the request may be sent via text message. The booking process enables the request state to be communicated to the voice-activated ambulance booking system.

Once the request for the ambulance enters the network, such as through a gateway, the user interface provided by the voice-activated ambulance booking system (i.e., the client) enters a waiting state, at step 512.

An available ambulance may be identified, at step 514. Several factors may be utilized to determine the availability of an ambulance, including the distance between the ambulance and the patient, traffic density, and the like.

In embodiments, at step 516, it may be determined whether a single ambulance was identified for a single client (i.e., patient) or multiple clients (i.e., patients) or whether multiple ambulances were identified for a single client.

It is determined, at step 518, if a single ambulance was identified for multiple clients or multiple ambulances were identified for a single client.

In a single ambulance identified for multiple clients embodiment, the voice-activated ambulance booking system utilizes the breathing, bleeding, and consciousness status of the patients, at step 520 to prioritize patients in the same locality.

Other factors corresponding to the user device may be utilized, at step 522, if there is more than one patient with the same priority. For example, the user device with the lowest remaining charge may be given priority so the patient can be located before the user device runs out of battery power. Similarly, the user device with the weakest signal strength may be given priority so the patient can be located before the signal drops or fails. Alternatively, the patient that is the farthest from the hospital may be given priority so the patient can be transported to the hospital while an alternative ambulance is identified for the patient that is closer to the hospital.

At step 524, the ambulance is assigned to the best suited patient (i.e., the patient that has the highest priority). Other patients may need to resend a request for an ambulance via voice commands or manually via the user interface.

In a multiple ambulance for a single client embodiment, all ambulances with requests from other patients are eliminated, at step 530, if the requests were made prior to the current request.

At step 532, the best suited ambulance is assigned to the patient. All other ambulances remain in or enter an available status.

In each embodiment (a single ambulance identified for multiple clients embodiment and a multiple ambulance for a single client embodiment) or if a single ambulance is identified for a single client, the ambulance sends an offer, along with an estimated time of arrival, to the user, at step 526.

The ambulance then enters a waiting status, at step 528. If the user acknowledges the offer, at step 534, before a timeout (i.e., a configurable period of time the user must accept the offer in before the offer expires), at step 536, the booking is confirmed, at step 542, and the ambulance remains in a busy status.

The user may track, at step 544, the ambulance in real-time, via the user interface of the voice-activated ambulance booking system, until it reaches its destination. Once the patient enters the ambulance, at step 546, the user is prompted to determine if the user and the patient are the same person. If the user and the patient are determined to be the same person, at step 548, the voice-activated ambulance booking system requests information corresponding to the patient from the database, at step 550. If the user and the patient are not determined to be the same person, at step 550, a missed call from the RMN of the patient is provided, at step 552, and the voice-activated ambulance booking system requests information corresponding to the patient from the database. In each case, the patient is transported to the hospital and friends and/or family of the patient is notified, at step 554.

If the user acknowledges the request, at step 534, but does not do so before a timeout, at step 536, the request expires, at step 538, and the ambulance enters an available status, at step 540, where it can be identified for a single patient or multiple patients, at step 516. If the user does not acknowledge the request, at step 534, the request expires, at step 538, and the ambulance enters an available status, at step 540, where it can be identified for a single patient or multiple patients, at step 516.

In practice, a request R1 may be received via text message (i.e., offline). A second request R2 may be received via an application (i.e., online). In cases where each request is prioritized the same, a tiebreaker may be used. Assume signal strength and batter percentage are low for the device sending request R1 as compared to the device sending request R2, request R1 receives higher priority and acceptance and acknowledgement of request R1 will be provided to user via text message.

In another example, a request R2 may be received via an application (i.e., online). A second request R2 may be received via text message (i.e., offline). In cases where each request is prioritized the same, a tiebreaker may be used. Assume signal strength and batter percentage are low for the device sending request R2 as compared to the device sending request R1, request R2 receives higher priority and acceptance and acknowledgement of request R2 will be provided to user via the application.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer storage media having computer-executable instructions embodied thereon that, when executed by a computer, causes the computer to perform operations for providing voice-activated ambulance booking, the operations comprising:
   receiving, at a user device in a locked state, a request from a user, the request initiating a workflow that enables the user to provide information about a patient to a booking engine;
   providing the workflow to the user, via a user interface of the user device while the user device is in the locked state, the workflow comprising a series of questions corresponding to a status of the patient;
   transmitting, from the user device to an ambulance booking system, via a network while the user device is the locked state, a request for an ambulance for the patient, the ambulance requested based on responses from the user, via the user interface of the user device, to the series of questions, and a detected location of the user device;
   determining, by the ambulance booking system, that a plurality of requests have been received from other patients and a single ambulance is available;
   obtaining, by the ambulance booking system, battery statuses of devices making the plurality of requests and/or signal strengths of devices making the plurality of requests;
   prioritizing, by the ambulance booking system, the plurality of requests based on the battery statuses of the devices making the plurality of requests and/or the signal strengths of the devices making the plurality of requests;
   assigning, by the ambulance booking system, the single ambulance to the patient or a patient of the other patients based on the prioritizing; and
   tracking the single ambulance in real-time, via the user interface, until it reaches the detected location of the user device.

2. The media of claim 1, wherein the request is a voice command from a user.

3. The media of claim 2, wherein the request is a text message.

4. The media of claim 3, further comprising communicating information of the patient to a health care facility that will receive the patient via the ambulance.

5. The media of claim 1, further comprising prioritizing requests from the patient and the other patients based on responses to the series of questions.

6. The media of claim 5, wherein the series of questions comprise breathing status, bleeding status, and/or consciousness status of the patient and the other patients.

7. A computerized method for providing voice-activated ambulance booking, the method comprising:
   receiving, at a user device in a locked state, a request from a user, the request initiating a workflow that enables the user to provide information about a patient to a booking engine;
   providing the workflow to the user, via a user interface of the user device while the user device is in the locked state, the workflow comprising a series of questions corresponding to a status of the patient;
   transmitting, from the user device to an ambulance booking system, view a network while the user device is the locked state, a request for an ambulance for the patient, the ambulance requested based on responses from the user, via the user interface of the user device, to the series of questions, and a detected location of the user device;
   determining, by the ambulance booking system, that a plurality of requests have been received from other patients and a single ambulance is available;
   obtaining, by the ambulance booking system, battery statuses of devices making the plurality of requests and/or signal strengths of devices making the plurality of requests;
   prioritizing, by the ambulance booking system, the plurality of requests based on the battery statuses of the devices making the plurality of requests and/or the signal strengths of the devices making the plurality of requests;
   assigning, by the ambulance booking system, the single ambulance to the patient or a patient of the other patients based on the prioritizing; and
   tracking the single ambulance in real-time, via the user interface, until it reaches the detected location of the user device.

8. The method of claim 7, further comprising determining a single ambulance is available.

9. The method of claim 7, further comprising assigning the single ambulance to the patient or a different patient of the other patients based on the prioritizing requests.

10. A system for providing voice-activated ambulance booking, the system comprising:
    a processor; and
    a computer storage medium storing computer-usable instructions that, when used by the processor, cause the processor to perform operations comprising:
       receiving, at a user device in a locked state, a voice command from a user, the voice command initiating a workflow that enables the user to provide information about a patient to a booking engine;
       providing the workflow to the user, via the user device while the user device is in the locked state, the workflow comprising a series of questions corresponding to a status of the patient;
       transmitting, from the user device to an ambulance booking system, via a network while the user device is the locked state, a request for an ambulance for the patient, the ambulance requested based on responses from the user, via the user device, to the series of questions, and a detected location of the user device;
       determining, by the ambulance booking system, that a plurality of requests have been received from other patients and a single ambulance is available;

obtaining, by the ambulance booking system, battery statuses of devices making the plurality of requests and/or signal strengths of devices making the plurality of requests;

prioritizing, by the ambulance booking system, the plurality of requests based on the battery statuses of the devices making the plurality of requests and/or the signal strengths of the devices making the plurality of requests;

assigning, by the ambulance booking system, the single ambulance to the patient or a patient of the other patients based on the prioritizing; and tracking the ambulance in real-time, via the user interface, until it reaches the detected location of the user device.

11. The system of claim 10, wherein the workflow is provided via a user interface of the user device.

12. The system of claim 10, wherein the workflow is provided via voice outputs of the user device.

13. The system of claim 10, wherein the workflow is provided via a combination of a user interface and voice outputs of the user device.

14. The system of claim 10, wherein the responses are received via voice commands.

* * * * *